United States Patent
Engels et al.

(10) Patent No.: US 11,641,868 B2
(45) Date of Patent: May 9, 2023

(54) SYNBIOTIC COMPOSITION FOR PREVENTING METABOLIC DISORDERS

(71) Applicant: N.V. NUTRICIA, Zoetermeer (NL)

(72) Inventors: Eefje Engels, Utrecht (NL); Cornelus Johannes Petrus Van Limpt, Utrecht (NL); Annemarie Oosting, Utrecht (NL); Akhtar Raish Oozeer, Utrecht (NL); Jan Knol, Utrecht (NL); Mona Mischke, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 16/730,525

(22) Filed: Dec. 30, 2019

(65) Prior Publication Data

US 2020/0253258 A1    Aug. 13, 2020

Related U.S. Application Data

(63) Continuation of application No. PCT/EP2018/067712, filed on Jun. 29, 2018.

(30) Foreign Application Priority Data

Jun. 30, 2017  (EP) .................................. 17179124

(51) Int. Cl.
| | |
|---|---|
| A61K 35/745 | (2015.01) |
| A61K 31/702 | (2006.01) |
| A23L 33/135 | (2016.01) |
| A23L 33/21 | (2016.01) |
| A23L 33/00 | (2016.01) |
| A61P 3/10 | (2006.01) |
| A61P 3/06 | (2006.01) |
| A61K 9/00 | (2006.01) |
| A61K 31/715 | (2006.01) |

(52) U.S. Cl.
CPC .............. *A23L 33/135* (2016.08); *A23L 33/21* (2016.08); *A23L 33/40* (2016.08); *A61K 9/0095* (2013.01); *A61K 31/702* (2013.01); *A61K 31/715* (2013.01); *A61K 35/745* (2013.01); *A61P 3/06* (2018.01); *A61P 3/10* (2018.01); *A23V 2002/00* (2013.01)

(58) Field of Classification Search
CPC ........ A23L 33/135; A23L 33/40; A23L 33/21; A61P 3/10; A61P 3/06; A61K 31/702; A61K 35/745; A23V 2002/00
See application file for complete search history.

(56) References Cited

U.S. PATENT DOCUMENTS

| | | | |
|---|---|---|---|
| 9,314,047 B2* | 4/2016 | Speelmans | A61P 37/02 |
| 9,386,793 B2 | 7/2016 | Blaser et al. | |
| 9,456,629 B2* | 10/2016 | Hougee | A61K 31/702 |
| 9,480,670 B2 | 11/2016 | Mace et al. | |

FOREIGN PATENT DOCUMENTS

| | | |
|---|---|---|
| EP | 2 143 341 A1 | 1/2010 |
| EP | 2 359 838 A1 | 8/2011 |
| EP | 2 452 571 A1 | 5/2012 |
| WO | WO-99/49877 A2 | 10/1999 |
| WO | WO-2006/091103 A2 | 8/2006 |
| WO | WO-2007/073194 A2 | 6/2007 |
| WO | WO-2008/116700 A1 | 10/2008 |
| WO | WO-2011/096808 A1 | 8/2011 |
| WO | WO-2012/153179 A1 | 11/2012 |
| WO | WO-2013/036102 A1 | 3/2013 |
| WO | WO-2013/054002 A1 | 4/2013 |
| WO | WO-2015/172191 A | 11/2015 |
| WO | WO-2016/020495 A1 | 2/2016 |
| WO | WO-2016/026684 A1 | 2/2016 |
| WO | WO-2017/043963 A1 | 3/2017 |
| WO | WO-2017/129649 A1 | 8/2017 |
| WO | WO-2017/145415 A1 | 8/2017 |

OTHER PUBLICATIONS

Karr et al. Epidemiology and Management of Hyperlipidemia. Am J Manag Care. 2017;23:S139-S148.*
Santos et al. Risk Factors for the Development of Atherosclerosis in Childhood and Adolescence. Arq Bras Cardiol. 2008;90(4):276-283.*
Swinburn et al. Dissecting Obesogenic Environments: The Development and Application of a Framework for Identifying and Prioritizing Environmental Interventions for Obesity. Preventive Medicine. 1999;29:563-570.*
Reuters. Overweight moms-to-be more likely to have obese kids. New York Post. 2016;1-7.*
Caudle A. Childhood obesity and familial hypercholesterolemia: genetic diseases that contribute to cardiovascular disease. Senior Honors Theses. 2014;457:1-38.*
Asemi, et al.; "Effect of multispecies probiotic supplements on metabolic profiles, hs-CRP, and oxidative stress in patients with type 2 diabetes"; Annals of Nutrition and Metabolism, vol. 63, No. 1-2, pp. 1-9; (2013).
Cani, et al.; "Selective increases of bifidobacterial in gut microflora improve high-fat-diet-induced diabetes in mice through a mechanism associated with endotoxaemia"; Diabetologia, vol. 50, pp. 2374-2383; (2007).
Eslamparast, et al.; "Effects of synbiotic supplementation on insulin resistance in subjects with the metabolic syndrome: a randomised, double-blind, placebo-controlled pilot study"; British Journal of Nutrition; vol. 112, pp. 438-445; (2014).
Grill, et al.; "Effects of Lactobacillus amylovorus and Bifidobacterium breve on cholesterol"; Letters in Applied Microbiology, vol. 31, pp. 154-156; (2000).
International Preliminary Report on Patentability issued in International Application No. PCT/EP2018/067703, dated Sep. 24, 2019.
International Preliminary Report on Patentability issued in International Application No. PCT/EP2018/067706, dated Jun. 21, 2019.

(Continued)

*Primary Examiner* — Lynn Y Fan
(74) *Attorney, Agent, or Firm* — N.V. Nederlandsch Octrooibureau

(57) ABSTRACT

The invention relates to improved liver health and lipid metabolism later in life upon ingestion of synbiotics early in life.

6 Claims, 2 Drawing Sheets

(56) References Cited

OTHER PUBLICATIONS

International Preliminary Report on Patentability issued in International Application No. PCT/EP2018/067712, dated Jun. 21, 2019.
International Search Report and Written Opinion issued in International Application No. PCT/EP2018/067703, dated Nov. 16, 2018.
International Search Report and Written Opinion issued in International Application No. PCT/EP2018/067706, dated Sep. 24, 2018.
International Search Report and Written Opinion issued in International Application No. PCT/EP2018/067712, dated Sep. 24, 2018.
Kondo, et al.; "Antiobesity Effects of Bifidobacterium breve Strain B-3 Supplementation in a Mouse Model with High-Fat Diet-Induced Obesity"; Biosci Biotechnol Biochem, vol. 74, No. 8, pp. 1656-1661; (2010).
Kuitunen, et al.; "Probiotics prevent IgE-associated allergy until age 5 years in cesarean-delivered children but not in the total cohort"; The Journal of Allergy and Clinical Immunology, vol. 123, No. 2, pp. 335-341; Feb. 2009.
Malaguarnera, et al.; "Bifidobacterium tongum with Fructo-Oligosaccharides in Patients with Non Alcoholic Steatohepatitis"; Digestive Diseases and Sciences, vol. 57, pp. 545-553; (2012).
Melanie, et al.; "Fermented inulin hydrolysate by Bifidobacterium breve as cholesterol binder in functional food application"; Conference Papers: International Symposium on Applied Chemistry (ISAC) 2016.
Mischke, et al.; "Specific synbiotics in early life protect against diet-induced obesity in adult mice"; Diabetes, Obesity and Metabolism, vol. 20, pp. 1408-1418; (2018).
Mofidi, et al.; "Synbiotic supplementation in lean patients with non-alcoholic fatty liver disease: a pilot, randomised, double-blind, placebo-controlled, clinical trial"; British Journal of Nutrition, vol. 117, No. 5, pp. 662-668; (2017).
Moroti, et al.; "Effect of the consumption of a new symbiotic shake on glycemia and cholesterol levels in elderly people with type 2 diabetes mellitus"; Lipids in Health and Disease, vol. 11, No. 29, pp. 1-8; (2012).
Ooi, et al.; "Cholesterol-Lowering Effects of Probiotics and Prebiotics: A Review of in Vivo and in Vitro Findings"; International Journal of Molecular Sciences, vol. 11, Issue 6, pp. 2499-2522; (2010).
U.S. Appl. No. 16/730,530, filed Dec. 30, 2019, Not yet assigned.
U.S. Appl. No. 16/730,538, filed Dec. 30, 2019, Not yet assigned.

* cited by examiner

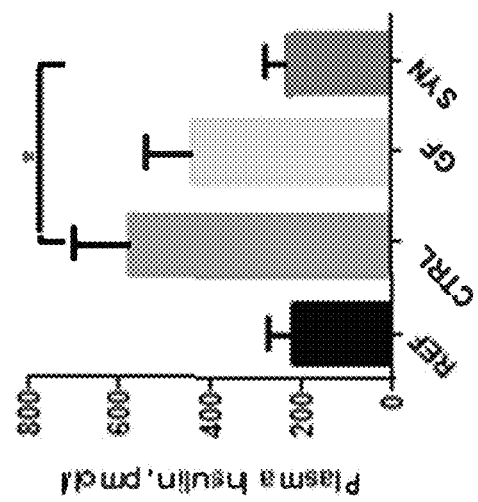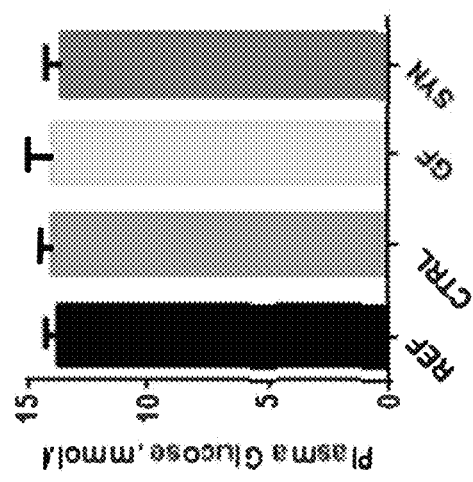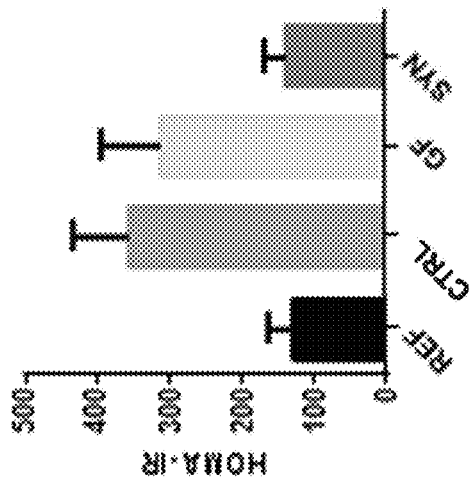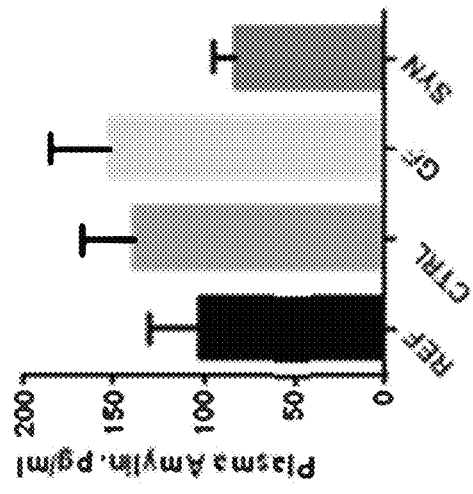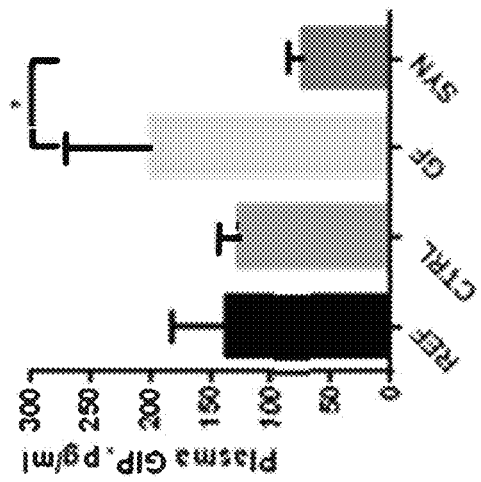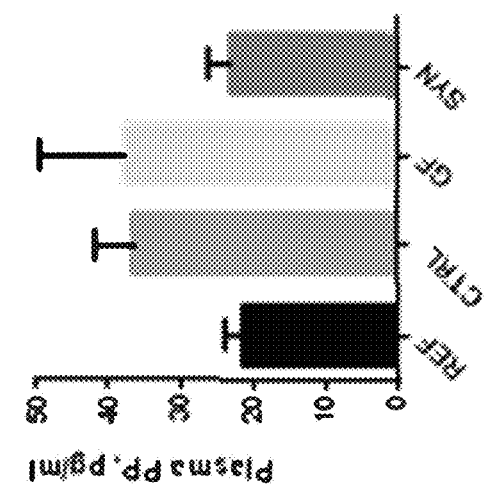

SYNBIOTIC COMPOSITION FOR PREVENTING METABOLIC DISORDERS

CROSS-REFERENCE TO RELATED APPLICATIONS

The present application is a Continuation of International Patent Application No. PCT/EP2018/067712, filed Jun. 28, 2018, and claims the benefit of priority to European Patent Application No. 17179124.7, filed Jun. 30, 2017, the entire contents of which are hereby incorporated by reference.

FIELD OF THE INVENTION

The present invention is in the field of nutritional compositions for infants and aims at preventing metabolic disorders later in life.

BACKGROUND OF THE INVENTION

Breast-feeding is the preferred method of feeding infants. It has been suggested that breast feeding early in life might influence the occurrence of disorders later in life. However, there are circumstances that make breast-feeding impossible or less desirable. In those cases infant formula and follow-on formula are a good alternative. The composition of modern infant or follow-on formulas is already highly adapted in such a way that it meets many of the special nutritional requirements of the fast growing and developing infant.

Still improvements can be made towards the constitution of infant milk formulae. Compared to breast fed infants formula fed infants have an increased risk of becoming obese, developing metabolic health diseases later in life, developing liver weight increase or non-alcoholic fatty liver disease (NFALD), or developing cardiovascular diseases later in life. Early in life feeding has a lasting programming effect on such disease risks in adulthood. These conditions are major health problems in the Western world and a leading preventable cause of death worldwide, with increasing prevalence in adults and children, and authorities view it as one of the most serious public health problems of the $21^{st}$ century. About 12 to 25% of people in the United States has NAFLD While NASH affects between 2 to 5% of people in the United States. It is estimated that Nonalcoholic fatty liver disease spectrum disorders affect approximately 1 billion individuals worldwide.

WO 2006/091103 describes a composition comprising *Bifidobacterium* and two non-digestible oligosaccharides to stimulate the intestinal flora of a human milk-fed infant.

WO 2013/036102 describes compositions with a specific fat component that has programming effects on the body and results in a reduced level of total blood cholesterol later in life when consuming a Western Style Diet thereby reducing the risk on western life style diseases.

U.S. Pat. No. 9,386,793 relates to therapeutic methods involving the use of probiotic Dorea, and optionally prebiotics, to restore a healthy mammalian bacterial intestinal microbiota.

WO 2011/096808 describes a composition comprising sialyl-oligosacharide and living *Bacteroides* ssp. to reduce the risk of overweight or obesity of an infant in later life.

SUMMARY OF THE INVENTION

The inventors surprisingly found, when employing animal models, that dietary supplementation with *Bifidobacterium breve* in combination with non-digestible oligosaccharides early in life resulted in later-in-life benefits. In particular it was found that later-in-life, after exposure to a Western Style Diet increased in calories and fat, the lipid metabolism was improved resulting in improved liver health, and improved plasma lipid parameters when compared to the control group that had not received this dietary intervention and was challenged with the Western Style Diet.

The inventors have found in a mouse model that it was possible to program the infants in such a manner that they could better withstand risks commonly associated with a Western Style Diet. When the infants received a diet supplemented with *Bifidobacterium breve* in combination with non-digestible oligosaccharides during their early life, it was found that excess liver weight gain was prevented. Fat accumulation in the liver, in particular triglycerides, later-in-life was reduced and ketone body formation, as determined by the amount of plasma beta-hydroxybutyric acid, was increased, both of which are indicative for reduced fat uptake and increased fat expenditure in the liver. Gene expression studies showed that in the group receiving the *B. breve* with non-digestible oligosaccharides early in life lipid metabolism and cholesterol biosynthesis pathways were changed compared to the control group, and more comparable to a healthy reference group not exposed to a Western Style Diet. Surprisingly the effects were not, or to a much lesser extent, observed in group that received only non-digestible oligosaccharides without *B. breve*.

Therefore the use of *B. breve* together with non-digestible oligosaccharides administered during infancy is particularly suitable to improve lipid metabolism later in live and to prevent lipid metabolism associated disorders, in particular fatty liver disease and/or hypercholesterolemia and/or plasma-cholesterol associated atherosclerosis.

DETAILED DESCRIPTION OF THE INVENTION

Thus the present invention concerns a method for preventing and/or reducing the risk of occurrence of disorders associated with impaired lipid metabolism selected from the group consisting fatty liver disease, hypercholesterolemia and plasma-cholesterol associated atherosclerosis later in life in a human subject by administering a nutritional composition comprising a combination of *Bifidobacterium breve* and non-digestible oligosaccharides early in life. Preferably the present invention concerns a method for preventing and/or reducing the risk of occurrence of disorders associated with impaired lipid metabolism selected from the group consisting hypercholesterolemia and plasma-cholesterol associated atherosclerosis later in life in a human subject by administering a nutritional composition comprising a combination of *Bifidobacterium breve* and non-digestible oligosaccharides early in life. In particular the present invention concerns a method for preventing and/or reducing the risk of occurrence of hypercholesterolemia and/or plasma-cholesterol associated atherosclerosis later in life in a human subject by administering a nutritional composition comprising a combination of *Bifidobacterium breve* and non-digestible oligosaccharides early in life.

In one embodiment, the present method is a non-medical method for preventing and/or reducing the risk of occurrence of disorders associated with impaired lipid metabolism selected from the group consisting fatty liver disease, hypercholesterolemia and plasma-cholesterol associated atherosclerosis later in life in a human subject by administering a nutritional composition comprising a combination of *Bifidobacterium breve* and non-digestible oligosaccharides early in life. Preferably the present invention concerns a non-medical method for preventing and/or reducing the risk of occurrence of disorders associated with impaired lipid metabolism selected from the group consisting of hypercholesterolemia and plasma-cholesterol associated atherosclerosis later in life in a human subject by administering a nutritional composition comprising a combination of *Bifidobacterium breve* and non-digestible oligosaccharides early in life. In particular the present invention concerns a non-medical method for preventing and/or reducing the risk of occurrence of hypercholesterolemia and/or plasma-cholesterol associated atherosclerosis later in life in a human subject by administering a nutritional composition comprising a combination of *Bifidobacterium breve* and non-digestible oligosaccharides early in life.

The invention can also be worded as the use of a combination of *Bifidobacterium breve* and non-digestible oligosaccharides for the manufacture of a nutritional composition for use in preventing and/or reducing the risk of occurrence of disorders associated with impaired lipid metabolism selected from the group consisting fatty liver disease, hypercholesterolemia and plasma-cholesterol associated atherosclerosis later in life in a human subject by administration of the nutritional composition to the human subject early in life. Preferably the present invention concerns the use of a combination of *Bifidobacterium breve* and non-digestible oligosaccharides for the manufacture of a nutritional composition for use in preventing and/or reducing the risk of occurrence of disorders associated with impaired lipid metabolism selected from the group consisting hypercholesterolemia and plasma-cholesterol associated atherosclerosis later in life in a human subject by administration of the nutritional composition to the human subject early in life. In particular the present invention concerns the use of a combination of *Bifidobacterium breve* and non-digestible oligosaccharides for the manufacture of a nutritional composition for use in preventing and/or reducing the risk of occurrence of hypercholesterolemia and/or plasma-cholesterol associated atherosclerosis later in life in a human subject by administration of the nutritional composition to the human subject early in life.

The invention can also be worded as a nutritional composition comprising a combination of *Bifidobacterium breve* and non-digestible oligosaccharides for use in preventing and/or reducing the risk of occurrence of disorders associated with impaired lipid metabolism selected from the group consisting fatty liver disease, hypercholesterolemia and plasma-cholesterol associated atherosclerosis later in life in a human subject by administration of the nutritional composition to the human subject early in life. Preferably the present invention concerns a nutritional composition comprising a combination of *Bifidobacterium breve* and non-digestible oligosaccharides for use in preventing and/or reducing the risk of occurrence of disorders associated with impaired lipid metabolism selected from the group consisting hypercholesterolemia and plasma-cholesterol associated atherosclerosis later in life in a human subject by administration of the nutritional composition to the human subject early in life. In particular the present invention concerns a nutritional composition comprising a combination of *Bifidobacterium breve* and non-digestible oligosaccharides for use in preventing and/or reducing the risk of occurrence of hypercholesterolemia and/or plasma-cholesterol associated atherosclerosis later in life in a human subject by administration of the nutritional composition to the human subject early in life.

In one embodiment, the present method or use is for use in preventing and/or reducing the risk of occurrence of fatty liver disease later in life. In one embodiment, the present method or use is for use in preventing and/or reducing the risk of occurrence of non-alcoholic fatty liver disease later in life.

In one embodiment, the present method or use is for use in preventing and/or reducing the risk of occurrence of hypercholesterolemia and/or plasma-cholesterol associated atherosclerosis later in life.

*Bifidobacterium breve*

The nutritional composition in the method or use according to the present invention, hereafter also referred to as the present (nutritional) composition, comprises *Bifidobacterium breve*. It was found that the presence of *B. breve* together with non-digestible oligosaccharides beneficially affected lipid metabolism and liver health later in life. *Bifidobacterium breve* is a Gram-positive, anaerobic, branched rod-shaped bacterium. The *B. breve* preferably has at least 95% identity with the 16 S rRNA sequence of the type strain of *B. breve* ATCC 15700, more preferably at least 97% identity (Stackebrandt & Goebel, 1994, *Int. J. Syst. Bacteriol.* 44:846-849). Preferred *B. breve* strains are those isolated from the faeces of healthy human milk-fed infants. Typically, these are commercially available from producers of lactic acid bacteria, but they can also be directly isolated from faeces, identified, characterised and produced. According to a preferred embodiment, the present composition comprises at least one *B. breve* selected from the group consisting of *B. breve* Bb-03 (Rhodia/Danisco), *B. breve* M-16V (Morinaga), *B. breve* R0070 (Institute Rosell, Lallemand), *B. breve* BR03 (Probiotical), *B. breve* BR92) (Cell Biotech), DSM 20091, LMG 11613, YIT4065, FERM BP-6223 and CNCM I-2219. Most preferably, the *B. breve* is selected from the group consisting of *B. breve* M-16V and *B. breve* CNCM I-2219, most preferably the *B. breve* is a M-16V. *B. breve* I-2219 was published a.o. in WO 2004/093899 and in U.S. Pat. No. 7,410,653 and was deposited at the Collection Nationale de Cultures de Microorganisms, Institute Pasteur, Paris, France on 31 May 1999 by Compagnie Gervais Danone. *B. breve* M-16V was deposited as BCCM/LMG23729 and is commercially available from Morinaga Milk Industry Co., Ltd.

The present composition preferably comprises viable *B. breve*. The present composition preferably comprises $10^4$ to $10^{12}$ colony forming units (cfu) *B. breve* per gram dry weight of the present nutritional composition, preferably $10^4$ to $10^{11}$, more preferably $10^5$ to $10^{10}$, most preferably from $10^6$ to $1\times10^9$ cfu *B. breve* per gram dry weight of the present composition. Preferably the composition comprises $10^4$ to $10^{13}$ cfu *B. breve* per 100 ml, more preferably $10^6$ to $10^{11}$ cfu *B. breve* per 100 ml, most preferably $10^7$ to $10^{10}$ cfu *B. breve* per 100 ml. In the context of the present invention, it is to be understood that the nutritional composition preferably does not comprise other probiotic bacteria, hence probiotic bacteria other than *Bifidobacterium breve* preferably are excluded from the nutritional composition in the method or use according to the present invention.

Non-Digestible Oligosaccharides

The nutritional composition in the method or use according to the present invention comprises non-digestible oligosaccharides (NDO). The term "oligosaccharide" as used in the present invention preferably refers to a saccharide with a degree of polymerization (DP) of 2 to 250, preferably a DP of 2 to 100, more preferably of 2 to 60. It is understood that in the context of this invention a saccharide with a DP in a certain range may include a mixture of saccharides with different average DP's, for example, if an oligosaccharide with a DP of 2 to 100 is included in the present composition, this may include compositions that comprise oligosaccharides with an average DP between 2 and 5, an average DP between 50 and 70 and an average DP between 7 and 60. The term "non-digestible oligosaccharide" as used in the present invention refers to oligosaccharides which are not or only partially digested in the intestine by the action of acids or digestive enzymes present in the human upper digestive tract (small intestine and stomach) but which are fermented by the human intestinal flora. For example, sucrose, lactose, maltose and maltodextrins are considered digestible. For example, galacto-oligosaccharides, fructo-oligosaccharides are considered non-digestible oligosaccharide.

Preferably the non-digestible oligosaccharides are soluble. The term "soluble" as used herein, when having reference to an oligosaccharide, means that the oligosaccharide is soluble according to the method described by L. Prosky et al., J. Assoc. Off. Anal. Chem. 71, 1017-1023 (1988).

The non-digestible oligosaccharide is preferably selected from the group consisting of fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides.

Preferably the present composition comprises fructo-oligosaccharides and/or galacto-oligosaccharides, more preferably galacto-oligosaccharides, most preferably transgalacto-oligosaccharides. In a preferred embodiment the composition comprises a mixture of galacto-oligosaccharides and fructo-oligosaccharides. Preferably the present composition comprises galacto-oligosaccharides with a DP of 2-10, preferably with an average DP between 2 and 10, and/or fructo-oligosaccharides with a DP of 2-60, preferably with an average DP between 2 and 60, preferably with an average DP between 10 and 60, preferably with an average DP between 15 and 60, preferably with an average DP between 20 and 60. The presence of non-digestible oligosaccharides in these preferred embodiments will have an improved effect on lipid metabolism and liver health later in life.

The galacto-oligosaccharide is preferably selected from the group consisting of transgalacto-oligosaccharides. In a particularly preferred embodiment the present method comprises the administration of transgalacto-oligosaccharides ([galactose]n-glucose; wherein n is an integer between 1 and 60, i.e. 2, 3, 4, 5, 6, ..., 59, 60; preferably n is selected from 2, 3, 4, 5, 6, 7, 8, 9, or 10). Transgalacto-oligosaccharides (TOS) are for example sold under the trademark Vivinal™ (Borculo Domo Ingredients, Netherlands). Preferably the saccharides of the transgalacto-oligosaccharides are 3-linked.

In one embodiment the nutritional composition in the method or use according to the present invention preferably comprises fructo-oligosaccharide. The term "fructo-oligosaccharide" as used herein refers to a non-digestible polysaccharide comprising a chain of at least 2 β-linked fructose units, with a DP of 2 to 250, preferably 7 to 100, more preferably 20 to 60. In one embodiment preferably inulin is used. Inulin is for example available under the tradename "Raftilin HP®", (Orafti). The average DP of the present fructo-oligosaccharide is preferably at least 7, more preferably at least 10, preferably below 100. The fructo-oligosaccharide used preferably has the (majority of) fructose units linked with a β(2→1) linkage. Other terms for fructooligosaccharides include inulin, fructopolysaccharide, polyfructose, fructans and oligofructose. The present composition preferably comprises fructo-oligosaccharides with a DP of 2 to 200.

In a preferred embodiment, the present composition comprises two or more non-digestible carbohydrates differing in monosaccharide unit composition, or differing in degree of polymerization (DP) or both. Two non-digestible carbohydrates differ in monosaccharide composition when there is at least 30 number % difference, more preferably at least 50 number % difference in monosaccharide composition based on total number of monosaccharide units. For instance galacto-oligosaccharides with an average composition of Glu-Gal3 and fructo-oligosaccharides with an average composition of Glu-Fru3 differ for 75 number %. Two non-digestible carbohydrates differ in DP if the average DP of the two carbohydrates differs more than 5 monosaccharide units, preferably more than 10 units, even more preferably more than 15 units. For example hydrolysed inulin with an average DP of 4 and long chain inulin with an average DP of 25 have a difference in DP of 21 units.

Preferably the present composition comprises galacto-oligosaccharides with an average DP between 2 and 10 and fructo-oligosaccharides with an average DP between 10 and 60. Preferably the present composition comprises fructo-oligosaccharides with an average DP between 2 and 10, and fructo-oligosaccharides with an average DP between 15 and 60. Preferably the present composition comprises galacto-oligosaccharides with an average DP between 2 and 10, and fructo-oligosaccharides with an average DP between 2 and 10. The presence of non-digestible oligosaccharides in these preferred embodiments will have an improved effect on lipid metabolism and liver health later in life.

Preferably the present composition comprises galacto-oligosaccharides and fructo-oligosaccharides in a weight ratio of 20 to 0.5, more preferably 20 to 1, most preferably from 12 to 2.

Preferably, the present composition comprises of 80 mg to 2 g non-digestible oligosaccharides per 100 ml, more preferably 150 mg to 1.50 g, even more preferably 300 mg to 1 g per 100 ml. Based on dry weight, the composition preferably comprises 0.25 wt. % to 20 wt. %, more preferably 0.5 wt. % to 10 wt. %, even more preferably 1.5 wt. % to 7.5 wt. % non-digestible oligosaccharides.

Preferably the present composition comprises $10^4$ to $10^{12}$ cfu *B. breve* per gram dry weight and 0.25 wt. % to 20 wt. % non-digestible oligosaccharides based on dry weight, more preferably $10^5$ to $10^{10}$ cfu *B. breve* per gram dry weight and 0.5 wt. % to 10 wt. % non-digestible oligosaccharides based on dry weight. Preferably the present composition does not comprise probiotic bacteria other than *Bifidobacterium breve*.

Preferably the present composition comprises $10^4$ to $10^{13}$ cfu *B. breve* and 80 mg to 2 g non-digestible oligosaccharides per 100 ml, more preferably $10^6$ to $10^{11}$ cfu *B. breve* and 300 mg to 1 g non-digestible oligosaccharides per 100 ml. Preferably the present composition does not comprise probiotic bacteria other than *Bifidobacterium breve*.

Preferably the present nutritional composition comprises i) $1\times10^5$ cfu to $1\times10^{10}$ cfu *B. breve* per gram dry weight, more preferably $1\times10^6$ cfu to $1\times10^{10}$ cfu; and either ii) 0.5 to 20 wt. % galacto-oligosaccharides based on dry weight, more preferably 0.5 to 10 wt. % galacto-oligosaccharides or iii) 0.05 to 2% fructo-oligosaccharides based on dry weight, more preferably 0.1 to 1 wt. % fructo-oligosaccharides or both ii) and iii). Preferably the present nutritional composition does not comprise probiotic bacteria other than *Bifidobacterium breve*.

Nutritional Composition

The nutritional composition in the method or use according to the present invention is preferably particularly suitable for providing the daily nutritional requirements to a human subject with an age below 36 months, particularly to a human subject with an age below 24 months, even more preferably to a human subject with an age below 18 months, most preferably to an infant below 12 months of age. Hence, the nutritional composition is for feeding or is used for feeding a human subject. The present composition preferably comprises a lipid, and a protein and a digestible carbohydrate component wherein the lipid component preferably provides 30 to 60% of total calories, the protein component preferably provides 5 to 20%, more preferably 5 to 15 wt. %, of the total calories and the digestible carbohydrate component preferably provides 25 to 75% of the total calories. Preferably the present composition comprises a lipid component providing 35 to 50% of the total calories, a protein component provides 6 to 12% of the total calories and a digestible carbohydrate component provides 40 to 60% of the total calories. The amount of total calories is determined by the sum of calories derived from protein, lipids and digestible carbohydrates.

The present composition is not human breast milk. The present composition preferably comprises vegetable lipids. The present composition preferably comprises other fractions, such as vitamins and minerals according to international directives for infant formulae. Preferably the nutritional composition is an infant formula, a follow on formula or a young child formula, more preferably an infant formula or a follow on formula.

Preferably the nutritional composition does not comprise Lactobacilli. *Lactobacillus* was found to be reduced in the group that had received *B. breve* and non-digestible oligosaccharides early in life and that had an improved lipid metabolism and liver health later in life.

In one embodiment the present composition is a powder suitable for making a liquid composition after reconstitution with an aqueous solution, preferably with water. Preferably the present composition is a powder to be reconstituted with water.

In order to meet the caloric requirements of the infant, the composition preferably comprises 50 to 200 kcal/100 ml liquid, more preferably 60 to 90 kcal/100 ml liquid, even more preferably 60 to 75 kcal/100 ml liquid. This caloric density ensures an optimal ratio between water and calorie consumption. The osmolarity of the present composition is preferably between 150 and 420 mOsmol/l, more preferably 260 to 320 mOsmol/l. The low osmolarity aims to reduce the gastrointestinal stress. Stress can induce adipocyte formation.

Preferably the present composition is in a liquid form, with a viscosity below 35 mPa·s, more preferably below 6 mPa·s as measured in a Brookfield viscometer at 20° C. at a shear rate of 100 $s^{-1}$. Suitably, the composition is in a powdered from, which can be reconstituted with water to form a liquid, or in a liquid concentrate form, which should be diluted with water. When the composition is in a liquid form, the preferred volume administered on a daily basis is in the range of about 80 to 2500 ml, more preferably about 450 to 1000 ml per day.

Use

Employing an animal model it was found that the combination of *B. breve* and non-digestible oligosaccharides, but not non-digestible oligosaccharides alone without *B. breve*, when administered early in life, beneficially affected parameters that are indicative for improved lipid metabolism and liver health later in life when compared to the control group that had not received this dietary intervention and was challenged with the Western Style Diet.

The present invention relates to a nutritional composition comprising *Bifidobacterium breve* and non-digestible oligosaccharides for use in improving lipid metabolism and liver health later in life in a human subject by administration of the nutritional composition to the human subject early in life.

A significant effect on preventing an excessive weight of the liver later in life when the mice were adult and after the mice were subjected to a Western Style Diet was observed. Likewise a significant reduction of liver triglycerides and a reduction of liver cholesterol was observed. This was observed at post-natal day 98, which is a time point corresponding to adulthood in humans. This indicates that early nutrition has a beneficial effect on liver weight gain, preventing excessive liver weight gain and prevention of unwanted liver conditions extending beyond the period in which it is actually administered. Furthermore, it was surprisingly found that subjects exhibited reduced fat accumulation, increased ketone body formation as indicated by effects on plasma beta-hydroxybutyrate and GIP levels. Increased ketone body formation upon fasting or exercise is indicative for an improved fast metabolic switch of carbohydrate oxidation to fat oxidation. Ketogenesis under increased or high dietary fat conditions can contribute to disposing of much of the fat that enters the liver, and dysfunction in this pathway could promote the development of NAFLD. Ketogenesis may play an important role in preventing diet-induced NAFLD. The control group that was exposed to a Western Style diet and had not received a synbiotic composition early in life leaned towards a NAFDL phenotype, indicated by the adverse effects on lipid homeostasis further supported by the effects on glucose homeostasis. Furthermore low-grade chronic inflammation is fundamental in the progression of NAFLD toward higher risk cirrhotic states.

Furthermore, gene expression study showed that the lipid pathways in the synbiotics group were more comparable to the healthy reference group than the control group exposed to Western Style Diet that had not received synbiotics early in life. Dysregulation of metabolic homeostasis, such as changes in insulin sensitivity or lipid metabolism, can be associated with the development of fatty liver disease (FLD). Hence NAFDL phenotype and fatty liver disease and its progression is prevented in the group that was administered synbiotics early in life.

Fatty liver disease comprises alcoholic fatty liver disease and non-alcoholic fatty liver disease (NAFLD). Preferably the present synbiotic composition is administered early in life for use in preventing or reducing the risk of occurrence later in life of NAFLD. NAFLD covers a spectrum of disease activity. This spectrum begins as fat accumulation in the liver (hepatic steatosis). A liver can remain fatty without disturbing liver function, but may also progress to become non-alcoholic steatohepatitis (NASH), a state in which steatosis is combined with inflammation and fibrosis (steatohepatitis). NASH is a progressive disease: over a 10-year period, up to 20% of patients with NASH will develop cirrhosis of the liver, and 10% will suffer death related to liver disease.

In one embodiment the present invention relates to a nutritional composition comprising *Bifidobacterium breve* and non-digestible oligosaccharides for use in preventing and/or reducing the risk of occurrence of liver weight increase and/or fatty liver disease later in life in a human subject by administration of the nutritional composition to the human subject early in life, more preferably for use in preventing and/or reducing the risk of occurrence of NAFLD.

A significant reduction in plasma cholesterol was observed later in life in the group that had received synbiotics early in life. Furthermore, gene expression studies showed that the cholesterol biosynthesis, storage, transport distribution and cell homeostasis in the synbiotics group were more comparable to the healthy reference group than the control group exposed to Western Style Diet that had not received synbiotics early in life. Reduced plasma levels of cholesterol are indicative for preventing or reducing the risk of occurrence of hypercholesterolemia and/or atherosclerosis. In one embodiment the present invention relates to a nutritional composition comprising *Bifidobacterium breve* and non-digestible oligosaccharides for use in reducing plasma cholesterol levels later in life, and/or for use in preventing and/or reducing the risk of of hypercholesterolemia and/or plasma-cholesterol associated atherosclerosis later in life, in a human subject by administration of the nutritional composition to the human subject early in life.

The present composition is to be administered to the human subject early in life. Early in life preferably relates to when the human subject has an age below 36 months, preferably when the human subject has an age below 24 months, even more preferably when the human subject has an age below 18 months, more preferably when the human subject is an infant with an age below 12 months, most preferably when the human subject is an infant with an age below 6 months. In one embodiment, the present composition is administered to a healthy human subject early in life, preferably to a term born human subject.

According to the present invention later in life means preferably when the human subject is a child or preferably an adult. Preferably later in life refers to when the human subject is at an age above 5 years, and more preferably above 18 years. Preventing later in life or reducing the risk of occurrence later in life is different from a direct preventive effect, an effect that occurs when consuming the nutritional intervention, in that it extends its health effect way further in life well after consumption of the nutritional composition has stopped, for example at least 2 years after administration of the formula has stopped, more preferably at least 4 years, more preferably at least 15 years. This later in life effect is believed to be due to a programming effect, wherein early in life, when the human subject is still growing and developing, the organs and its metabolic capacity (such as adipocyte formation, pancreatic B cell mass formation, liver development) are programmed during a critical window early in life, and effects happening at this time period have a health effect later in life. Indeed microbiota transfer at postnatal day 42 had no effect on metabolic health indicating that the critical window had passed in the mice.

In a preferred embodiment the nutritional composition comprising *B. breve* and non-digestible oligosaccharides is to be used in human subjects that exposed to or raised in an obesogenic environment and/or that consumes after infancy a Western Style Diet. A Western Style Diet is increased in fat and is increased in saturated fatty acids, with the fat providing more than 35% of the total calories of the diet, and with the saturated fatty acids providing more than 10% of the total calories of the diet. The term obesogenic environment refers to an environment that promotes gaining weight and to an environment that is not conducive to weight loss within the home or workplace (Swinburn, et al., 1999, Prev Med 29:563-570). In other words, the obesogenic environment refers to an environment that promotes, induces, helps, or contributes to, obesity. Factors that contribute are urbanization, often accompanied by a reduction in physical activity, and easy access to food. In one embodiment, the nutritional composition is of particular benefit for infants that are exposed to an environment wherein the average diet is a Western Style Diet that is increased or high in fat and is increased or high in saturated fatty acids, with the fat providing more than 35% of the total calories of the diet, and with the saturated fatty acids providing more than 10% of the total calories of the diet, more in particular a Western Style Diet that is characterised as comprising fat providing between 35 and 45% of the total calories of the diet and comprising saturated fatty acids providing between 10 and 20% of the total calories of the diet.

In a preferred embodiment the human subject is at risk of developing disorders related to an impaired lipid metabolism or impaired liver health, later in life. Therefore the human subject is preferably selected from the group consisting of a preterm infant, a small for gestational age infant, a large for gestational age infant, an infant born form an overweight or obese mother, an infant born from a mother suffering from diabetes type 2 or gestational diabetes, an infant born by C-section and an infant that is being treated or has been treated with antibiotics.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

BRIEF DESCRIPTION OF THE DRAWINGS

FIGS. 2A-2F show plasma markers for glucose homeostasis at adulthood after early in life nutritional intervention. Data are mean±SEM. *$p \leq 0.05$, **$p \leq 0.01$. Systemic markers for glucose homeostasis: homeostatic model assessment insulin resistance, HOMA-IR (FIG. 2A), glucose (FIG. 2B), insulin (FIG. 2C), amylin (FIG. 2D), gastric inhibitory polypeptide, GIP (FIG. 2E) and pancreatic polypeptide, PP (FIG. 2F). SYN: group that received *B. breve* and non-digestible oligosaccharides early in life, followed by a Western Style Diet on day 42-98. G/F: group that received non-digestible oligosaccharides early in life, followed by a Western Style Diet on day 42-98. CTR: group that received no B. breve and no non-digestible oligosaccharides early in life, followed by a Western Style Diet on day 42-98. REF: control group that was raised on standard chow without early in life nutritional intervention or a later in life Western Style Diet challenge.

Figure 1A:
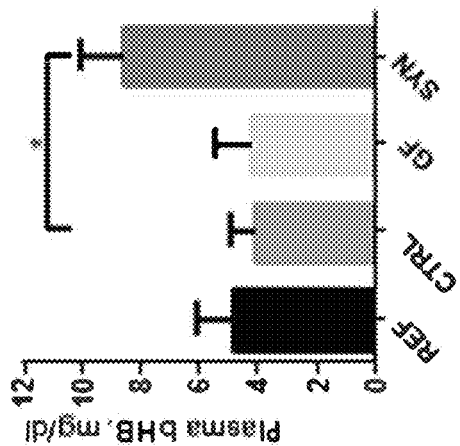
FIGS. 1A-1F show plasma markers for lipid metabolism and hepatic parameters at adulthood after early in life nutritional intervention. Data are mean±SEM. *$p \leq 0.05$, **$p \leq 0.01$. Systemic markers for lipid homeostasis: beta-hydroxybuturate, bHB (FIG. 1A), total cholesterol, TC (FIG. 1B), triglycerides, TG (FIG. 1C). Hepatic markers: liver weight (FIG. 1D), liver TC (FIG. 1E) and liver TG (FIG. 1F). SYN: group that received *B. breve* and non-digestible oligosaccharides early in life, followed by a Western Style Diet on day 42-98. G/F: group that received non-digestible oligosaccharides early in life, followed by a Western Style Diet on day 42-98. CTR: group that received no *B breve* and no non-digestible oligosaccharides early in life, followed by a Western Style Diet on day 42-98. REF: control group that was raised on standard chow without early in life nutritional intervention or a later in life Western Style Diet challenge.
Figure 1B:
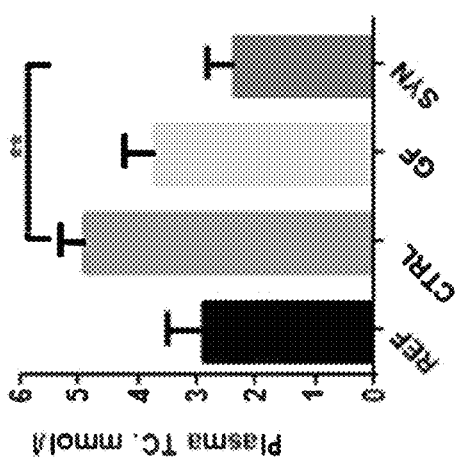
Figure 1C:
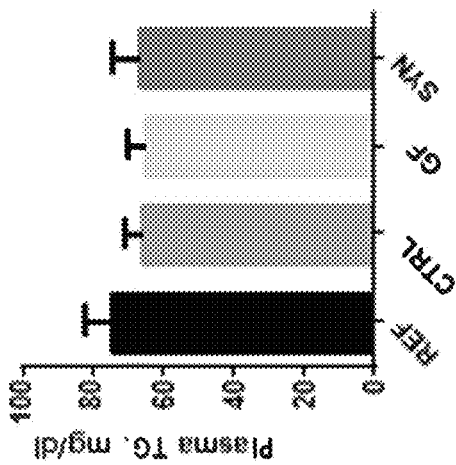

EXAMPLE 1: LATER IN LIFE PLASMA AND LIVER SIGNATURES INDICATIVE FOR LIPID HOMEOSTASIS AND LIVER HEALTH ARE BENEFICIALLY AFFECTED BY SYNBIOTICS INTERVENTION IN EARLY LIFE

Material & Methods

Mice were housed in Macrolon type 2 cages under controlled standard housing conditions and food and water ad libitum. Female and male C57BL/6J mice were obtained from Harlan Laboratories B.V., The Netherlands, and time-mated. On postnatal day (PN)2, litters were culled and four males and two female pups were randomly assigned perdam. During adaptation, pregnancy and lactation, animals were fed an irradiated standard semi-synthetic diet appropriate for breeding according to the recipe of the American Institute of Nutrition (AIN-93G; 16.4 kcal % fat, 18.8 kcal % protein; RDS, The Netherlands). On PN2, lactating dams were assigned to different intervention diets, i.e. different supplementations of the AIN-93G diet, either with non-digestible oligosaccharides [G/F: 2% w/w scGOS (short chain galactooligosaccharides (Vivinal® GOS)): lcFOS (long chain fructo-oligosaccharides (Inulin HP®)) w/w 9:1], synbiotics [SYN: (2% w/w G/F+$10^9$ cfu/g Bifidobacterium breve M-16V (Morinaga Milk Industries Ltd.)] or vehicle control (CTRL: 2% w/w maltodextrin). In addition to the supplementation of the diets, the pups received daily (PN10-15) an oral dose (30 µl) as drops of respective supplement (G/F and maltodextrin approx. 10-15 mg/day, $1\times10^9$ cfu B. breve M-16V). After weaning (PN21), the male offspring was housed in pairs and continued on respective supplemented intervention diet until PN42, a period corresponding with infancy and early childhood in humans. After PN42 until PN98, during adolescence and adulthood, the CTRL, G/F and SYN animals were fed a Western Style Diet (WSD; AIN-93G diet with an adjusted lipid fraction containing 20 wt. % lipid (17 wt. % lard, 3 wt. % soy oil, 0.1 wt. % cholesterol), representing a mild Western Style Diet providing about 40% of the total calories in fat and which contained about 14.5% saturated fatty acids based on total calories) as challenge. This diet has an increased level of fat based on total energy and an increased percentage of saturated fatty acids compared to what is considered healthy. From PN21 onwards, food intake was determined at continuous intervals by weighing the difference between provided and remaining food.

On PN98, after 6 h fasting, the animals were euthanized by isofluran/02 anesthesia followed by cervical dislocation. Blood samples were collected in $K_3$EDTA-coated microtubes (Greiner Bio-one, Germany). Plasma was obtained from blood samples by centrifugation (1350 g, 10 min, 4° C.) and subsequently snap frozen in liquid nitrogen and stored at −80° C. Liver was collected during dissection, weighed, snap frozen in liquid nitrogen and stored at −80° C. until further analysis.

In PN98 plasma samples, fasting plasma total cholesterol (Plasma TC; cholesterol liquicolor CHOD-PAP, Instruchemie, Delfzijl, The Netherlands), triglycerides (Plasma TG; GPO trinder method, Sigma Aldrich, Zwijndrecht, The Netherlands), beta-hydroxybutyrate (Plasma bHB; 3-Hydroxybutyrate LiquiColor, Stanbio Laboratory, Boerne, Tex., USA) and glucose (GOD-PAP method, Roche diagnostics, Almere, The Netherlands) were measured colorimetrically by using a microplate imaging system (Bio-Rad Laboratories Inc., Hercules, Calif., USA). Fasting plasma insulin, amylin, glucose-dependent insulinotropic polypeptide (GIP), and leptin were measured simultaneously using a multiplex approach (MILLIPLEX MAP Mouse Metabolic Hormone Magnetic Bead Panel, Merck KGaA, Darmstadt, Germany). Samples, controls and standards were prepared according to manufacturer's protocol and fluorescence was quantified using a Bio-Plex™ 200 Luminex instrument (Bio-Rad Laboratories Inc., Hercules, Calif., USA). As indirect measure of insulin sensitivity, the homeostasis model assessment of insulin resistance (HOMA-IR; [glu (mmol/l)*ins (pmol/l)/22.5]) was applied for fasting plasma glucose and insulin. In liver tissue from PN98, protein (BCAtm Protein Assay Kit, Thermo scientific, Breda, the Netherlands), triglyceride (Triglycerides liquicolor mono kit, Human Diagnostics, Wiesbaden, Gemany) and cholesterol (Cholesterol liquicolor mono kit, Human Diagnostics, Wiesbaden, Germany) content were assessed colorimetrically, using a microplate imaging system (Bio-Rad Laboratories Inc., Hercules, Calif., USA).

Total RNA from duodenum, jejunum, ileum, colon, liver and WAT was isolated, purified and immediately stored at −80° C. For this purpose, DNAse treated TRIzol/chloroform (Invitrogen, Breda, The Netherlands) and the RNAeasy mini kit (Qiagen, Venlo, The Netherlands) were used according to manufacturers' instructions. The RNA was quantified (NanoDrop ND-1000 UV-vis spectrophotometer, Isogen, Maarsen, The Netherlands) and its integrity was verified with the 6000 Nano Kit using the Eukaryote Total RNA Nano assay according on the Agilent 2100 Bioanalyzer (Agilent Technologies, Amsterdam, The Netherlands). If samples showed intact bands of 18S and 28S ribosomal RNA subunits, displayed no chromosomal peaks or RNA degradation products and had a RNA integrity number (RIN) above 8.0, they were considered suitable for hybridization to the microarray.

Labelled cDNA was prepared from 100 ng purified RNA per sample using the Ambion Whole Transcript (WT) Expression kit (Life Technologies, Carlsbad, USA) and Affymetrix GeneChip VVT Terminal Labelling kit (Affymetrix, Santa Clara, USA). All samples of one tissue were hybridized to the same Affymetrix GeneChip Mouse Gene 1.1 ST array according to manufacturer's protocols. Integrated in an on-line pipeline, Bioconductor software packages were used to perform quality control and normalisation steps {Lin, 2011 #287}. Applying robust multiarray (RMA) analysis algorithm from the Bioconductor library AffyPLM with default settings, normalised expression estimates of probe sets were computed {Irizarry, 2003 #275}. According to Dai et al. {Dai, 2005 #263}, probe sets were redefined and assigned to unique gene identifiers (IDs) of the Entrez Gene database, resulting in 21,187 assigned Entrez IDs.

To reduce numbers of variables, only genes with an intensity value of >20 on at least 5 arrays and an interquartile range >0.1 were selected for further analysis, resulting in 14,230 genes for liver, 15,574 genes for WAT, 14,377 genes for colon, 15,467 genes for duodenum, jejunum and ileum. Using intensity based-moderated t-statistics (IBMT) implementing empirical Bayes correction {Sartor, 2006 #313}, signal 2 log ratios and respective fold changes (2 log ratio of 1 equals a fold change of 2), and related significances of change were calculated from the mean signal intensities of the four groups. Resulting fold changes and corresponding p-values were applied for descriptive bioinformatic analysis and visualisation of the data.

To relate the gene expression data to biological functions and canonical pathways, Ingenuity Pathway Analysis (IPA, IngenuityH Systems, www.ingenuity.com) was applied using p=0.05 as filter for genes to perform comprehensive pathway and network analysis on.

The REF group represent the control group that did not receive the diet intervention (early life phase) and did not receive the WSD challenge diet (later life). In the statistical analyses, the three WSD-challenged groups (CTRL, G/F, SYN) were compared. Statistical analyses were performed using IBM SPSS Statistics 19.0 (SPSS Benelux, Gorinchem, The Netherlands) and GraphPad Prism 6 (GraphPad Software, La Jolla, Calif., USA). All variables were tested for normal distribution using the One-Sample Kolmogorov-Smirnov Test. If normally distributed, variables were analyzed in CTRL vs. G/F vs. SYN by one-way ANOVA. On significant effects, post hoc analysis using Tukey's multiple comparisons test was performed to compare between the individual groups. In case of non-Gaussian distribution, a log-transformation was performed preceding the one-way ANOVA analysis. Differences were considered significant with p≤0.05. Data are presented as mean±SEM unless otherwise indicated.

Results

Early life nutritional intervention with either G/F or SYN compared to control diet (REF and CTRL group) did not affect developmental growth during and directly after the intervention period until PN42. Body weight, fat mass, and lean body mass did not differ between the experimental groups at this time point. Also fat mass relative to body weight (fat mass %) was similar in all groups. Upon challenge with WSD of CTRL, G/F and SYN groups from PN42 to PN98, animal length, and lean body mass remained similar in all groups, indicating a normal growth trajectory. Neither in the early life (PN21-42) nor in the later life period (PN42-93), differences in food intake between groups were detected that could account for observed phenotypes.

Results on markers for systemic and liver lipid metabolism are shown in FIG. 1. Plasma beta-hydroxybutyric (bHB) acid, was significantly increased in the SYN group (FIG. 1A). bHB is an energy source during fasting or exercise, as well as a signaling molecule in the lipid homeostasis, and indicative for ketone formation. It is also indicative for an increased expenditure of fatty acids by beta-oxidation e.g. in the liver. It is indicative for an improved metabolic switch to fat oxidation when fasting. Also plasma cholesterol was significantly lower (p=0.007) in the SYN group, with an intermediate effect in the G/F group (FIG. 1B), when compared with CTRL. There were no significant effects on plasma TG (FIG. 1C).

Figure 1D:
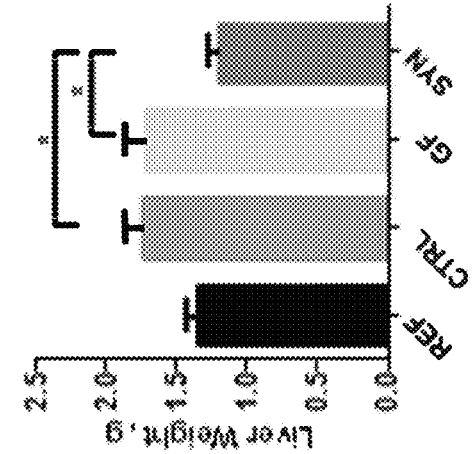
Figure 1E:
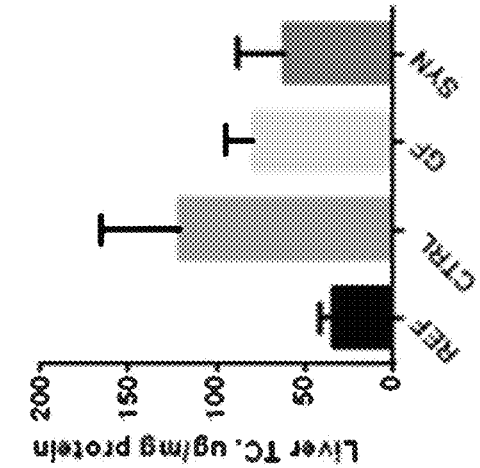
Figure 1F:
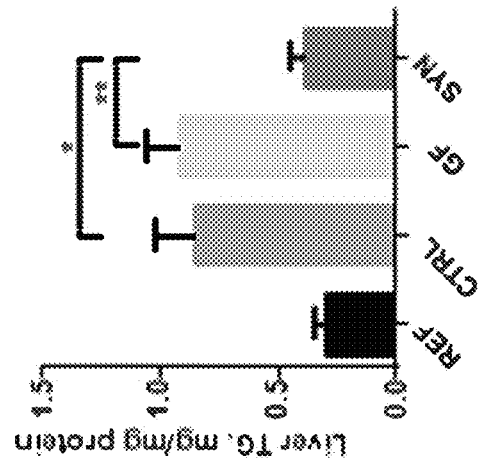

Dysregulation of metabolic homeostasis, such as changes in lipid metabolism, is associated with the development of fatty liver disease (FLD), a reversible condition of ectopic fat accumulation in the liver. Hence, relevant liver parameters were measured. The average liver weight of SYN animals on dissection was with significantly lower compared to CTRL and G/F animals (FIG. 1D). Differences in liver total cholesterol relative to the liver protein were trend-wise lower (p=0.08), and followed the stair-like visual pattern (FIG. 1E). Liver triglyceride content of SYN was significantly lower than in CTRL and G/F (FIG. 1F).

FIG. 2 shows the effect of glucose metabolism, as this may influence lipid metabolism and liver health. HOMA-IR calculation was based on fasted plasma glucose and insulin levels, of which the former was—unsurprisingly—similar in all groups and the latter was significantly different (p=0.039), with CTRL, G/F and SYN showing a stair-like descending pattern. HOMA-IR was lower in SYN than in CTRL and hence indicated a more sensitive insulin response of the organism. While fasted plasma glucose levels (FIG. 2B) are similar in all groups, the HOMA-IR (FIG. 2A), which is an index for insulin sensitivity, and various signalling molecules relevant for the glucose homeostasis, including insulin (FIG. 2C), amylin (FIG. 2D), GIP (FIG. 2E) and PP (FIG. 2F), show improved (trend-wise) plasma levels in SYN after WSD challenge on PN98, with plasma insulin in SYN being significantly lower than in CTRL. Plasma GIP, a potent incretin that is also known to affect glucose uptake and lipid synthesis, was similarly high in all groups expect for SYN, which was significantly lower than G/F (p=0.014).

The effects on lipid homeostasis, indicate that the CTRL group leans towards a NAFDL phenotype, and this is further supported by the effects on glucose homeostasis. Furthermore low-grade chronic inflammation is fundamental in the progression of NAFLD toward higher risk cirrhotic states. Hence NAFDL phenotype and fatty liver disease is prevented/rescued in SYN.

To identify potential molecular mechanisms underlying the beneficial effects of early life synbiotic supplementation, we performed microarray analysis from six relevant tissues; duodenum, jejunum, ileum and colon, liver and white adipose tissue. For SYN vs. CTRL, we observed the strongest effect, determined as numbers of significantly (p<0.05) differentially expressed genes, in the ileum (n=1592) followed by jejunum (n=1307) and duodenum (n=1227). 1191 genes were significantly regulated in liver, while expression of only 315 and 285 genes was significantly different in WAT and colon, respectively. In all analyzed tissues, similar numbers of genes with absolute fold change higher than 1.2 in SYN versus CTRL comparison were either up- or down-regulated, accounting in small intestine and colon for the bulk of regulated genes. However, in liver and WAT the expression of majority of genes was regulated with absolute fold change lower than 1.2, indicating that synbiotic supplementation compared with CTRL induces weaker regulation in liver and WAT.

Comparison of differentially expressed genes in ileum, jejunum and duodenum revealed that only 84 genes, which account for less than 10% of the differentially expressed genes per segment, were shared between the tissues. This indicates that early life synbiotic supplementation induces long-term tissue-specific transcriptional responses in intestinal segments when compared with CTRL. Notably, all overlapping genes changed gene expression in the same direction in all segments of the small intestine, with 69 being up- and the rest down-regulated. Annotation of the 84 genes using GO description identified 17 and 12 genes indicated in metabolic and immune functions, respectively.

To identify biological functions and canonical pathways that are specifically targeted by the differential regulation of genes, we used Ingenuity Pathway Analysis (IPA). In IPA the significance of regulation is based on the number and change of regulated genes in relation to the total number of genes attributed to a function. In the ileum, biological functions and canonical pathways were strongly regulated with the top 5 having −log(p-values) between 14.25-11.98 and 12.80-5.27, respectively. In liver the regulation of biological functions and pathways had maximal −log(p-value) of 7.49 and 3.04. In the ileum the strongest regulated biological function was "Lipid Metabolism", and the strongest regulated canonical pathway was "Cholesterol Biosynthesis". Zooming in on cholesterol metabolism, it was found that gene sets related to biosynthesis (mevalonate pathway, steroid biosynthesis), cholesterol uptake into the cell and regulation of homeostasis were up-regulated in mice supplemented with SYN in early life, while gene sets related cholesterol storage, excretion and distribution were rather down-regulated, which might indicate a higher cholesterol need of the cells. These regulations were largely in line with the REF group. However, in the G/F group these effects were not, or to a lesser extent, present, and the results were more comparable to the CTRL group.

EXAMPLE 2: MICROBIOTA MODULATION ALONE DOES NOT RESULT IN LONG TERM EFFECT ON METABOLIC HEALTH

Germ-free C57/Bl6 male mice maintained on autoclaved standard chow were used for transplantation. On week 5, all the mice were acclimatized to sterile WSD for 1 week. Frozen contents from cecum of chow (CTRL) and synbiotic (SYN) supplemented mice (collected at PN42 from feeding experiment) were homogenized in PBS buffer supplemented with reducing solution (0.02M Na2S and 1% cystein dissolved in $NaHCO_3$ buffer). Two separate donors from each group were selected. Following one week of acclimatization, mice (6 weeks old, PN42, 4-5 mice per group) were fasted for 4 h and gavaged with the resultant slurry (200 μl). Transplanted mice were maintained in autoclaved individual ventilated cages with sterile bedding and fed sterile WSD and autoclaved water ad libitum for 14 weeks. Body weight was measured and whole body magnetic resonance imaging (MRI) was performed on PN 42, 43, 70 and 98.

At the time of transfer (PN42), there were no differences in the body weight, fat mass and lean body mass between recipient GF mice. Following microbiota transfer, we observed no significant differences in body weight, fat mass and lean body mass between CTRL and SYN groups for diet*time interaction. Thus, the altered microbiota following synbiotic supplementation is not sufficient to transfer the beneficial phenotype of synbiotic-supplemented mice to recipients. It indicates that it is rather the actual process of early life microbiota modulation by the presence of non-digestible oligosaccharides and *B. breve* early in life in the gut that can be considered necessary to induce a long term metabolic health effect.

The invention claimed is:

1. A method of reducing the risk of occurrence of hypercholesterolemia and/or plasma-cholesterol associated atherosclerosis in a human subject above 5 years of age, comprising administering to the human subject when 0 to 36 months of age a nutritional composition, comprising *Bifidobacterium breve* and a mixture of galacto-oligosaccharides and fructooligosaccharides, wherein the nutritional composition is an infant formula or follow on formula or young child formula, wherein the human subject is at increased risk of developing hypercholesterolemia and/or plasma-cholesterol associated atherosclerosis due to being an infant born from an overweight or obese mother with a BMI higher than or equal to 25 and/or an infant born from a mother suffering from diabetes type 2 or gestational diabetes and wherein the human subject consumes after infancy a Western Style Diet that is increased in fat and is increased in saturated fatty acids, with the fat providing more than 35% of the total calories of the diet, and with the saturated fatty acids providing more than 10% of the total calories of the diet.

2. The method according to claim 1 wherein the composition is administered to the human subject when 0 to 12 months of age.

3. The method according to claim 1, wherein the risk of occurrence of hypercholesterolemia and/or plasma-cholesterol associated atherosclerosis is reduced when the human subject is above 18 years of age.

4. The method according to claim 1, wherein the *Bifidobacterium breve* is *Bifidobacterium breve* M-16V.

5. The method according to claim 1, wherein the nutritional composition is an infant formula or follow on formula.

6. The method according to claim 1, wherein the nutritional composition comprises $10^4$ to $10^{12}$ cfu *Bifidobacterium breve* per gram dry weight of the nutritional composition and 0.25 to 20 wt % of the mixture of galacto-oligosaccharides and fructooligosaccharides based on dry weight of the nutritional composition.

* * * * *